(12) United States Patent
Koch et al.

(10) Patent No.: US 6,452,055 B1
(45) Date of Patent: Sep. 17, 2002

(54) METHOD FOR THE CATALYTIC HYDROFORMYLATION OF OLEFINS IN A MICROEMULSION

(75) Inventors: Herbert Koch, Raesfeld; Reinhard Schomaecker; Marco Haumann, both of Berlin, all of (DE)

(73) Assignee: Sasol Germany GmbH (DE)

( * ) Notice: Subject to any disclaimer, the term of this patent is extended or adjusted under 35 U.S.C. 154(b) by 0 days.

(21) Appl. No.: 09/700,827
(22) PCT Filed: May 21, 1999
(86) PCT No.: PCT/DE99/10521
§ 371 (c)(1),
(2), (4) Date: Jan. 5, 2001
(87) PCT Pub. No.: WO99/61401
PCT Pub. Date: Dec. 2, 1999

(30) Foreign Application Priority Data

May 25, 1998 (DE) .......................... 198 22 968

(51) Int. Cl.$^7$ ............................................... C07C 45/50
(52) U.S. Cl. ........................................ 568/454; 568/451
(58) Field of Search ................................. 568/451, 454

(56) References Cited

U.S. PATENT DOCUMENTS

| 2,237,066 A | 4/1941 | Weisberg et al. |
| 4,399,312 A | 8/1983 | Russell et al. |
| 4,483,802 A | 11/1984 | Gaertner et al. |
| 4,523,036 A | 6/1985 | Cornils et al. |

FOREIGN PATENT DOCUMENTS

| EP | 0308154 | 8/1990 |

OTHER PUBLICATIONS

B. Fell and G. Papadogianakis: "Rhodiumkatalysierte mizellare Zweiphasenhydroformylierung von n–Tetradecen–1 mit grenzflaechenaktiven Sulfobetainderivaten des Tris(2–pyridyl)phosphans als wasserloesliche Komplexliganden," *J.ournal of Molecular Catalysis*, 66 (1991), pp. 143–154.

B. Fell, C. Schobben, and G. Papadogianakis: "Hydroformylierung homologer w–Alkencarbonsaeureester mit wasserloeslichen Rhodiumcarbonyl/tert. Phosphan–Komplexkatalysatorsystemen," *Journal of Molecular Catalysis A: Chemical* 101 (1995), pp. 179–186.

*Primary Examiner*—Sreeni Padmanabhan
(74) *Attorney, Agent, or Firm*—Browning Bushman P.C.

(57) ABSTRACT

This invention relates to a process for the catalytic hydroformylation of olefins by reaction of an olefin with hydrogen and carbon monoxide in a liquid, aqueous-organic reaction medium in the presence of a water-soluble hydroformylation catalyst, characterized in that for a substantial period of the hydroformylation reaction, the aqueous-organic medium is present in the form of a microemulsion, which is made up of an oil phase containing the olefin or the olefin and its hydroformylation products, an aqueous phase containing the water-soluble complex catalyst, and a nonionic surfactant.

15 Claims, No Drawings

METHOD FOR THE CATALYTIC HYDROFORMYLATION OF OLEFINS IN A MICROEMULSION

This Application is a 371 of PCT/DE99/10521 filed May 21, 1999 now WO 99/61401 published Dec. 2, 1999.

BACKGROUND OF THE INVENTION

1. Field of the Invention

The present invention relates to a process for the catalytic hydroformylation of olefins using carbon monoxide and hydrogen, wherein the hydroformylation reaction is carried out in a microemulsion.

2. Description of the Prior Art

In 1938, Otto Roelen studied the effects of olefins, specifically ethylene, on the Fischer-Tropsch synthesis in the laboratories of Ruhrchemie AG, Oberhausen. Roelen construed small amounts of propanol and diethyl ketone as products of a novel chemical reaction, namely hydroformylation (cf. DE 849 548, U.S. Pat. No. 2,237,066).

In the middle of the 1950s, this conversion of an alkene into an n-aldehyde and the isomeric iso-aldehyde, now known as the oxo synthesis over a transition metal catalyst, gained increasing economic importance.

Two factors were primarily responsible for this development: on the one hand, innovations in the petrochemical industry made it possible to produce the olefins in a sufficient amount with consistently high quality and at a favorable price and, on the other hand, the products of the hydroformylation were needed as intermediates in the production of PVC and detergents, two rapidly growing markets which even today are still the main outlets for hydroformylation products.

The first-generation catalysts contained only cobalt as a catalyst metal (BASF, ICI, Ruhrchemie). Owing to the high stability of the cobalt carbonyls, extreme reaction conditions were required: pressures of from 200 to 300 bar, temperatures of from 150° C. to 180° C. (H. Bahrmann, H. Bach, *Oxo Synthesis,* Ullmann, $5^{th}$ ed., Vol. A 18, p. 321).

In the middle of the 1960s, the Shell process for the first time employed phosphine ligands in place of carbon monoxide, whereby the n:iso ratio could be increased. In addition, the reaction conditions were far less severe.

With the second generation of catalysts, this ligand modification was combined with the replacement of the cobalt central atom by rhodium. Modified rhodium catalysts allowed far milder reaction conditions, achieved higher n:iso ratios, and reduced the hydrogenation of the alkene as an undesirable secondary reaction. These processes, known as low-pressure oxo (LPO) processes, have been superseded at the beginning of the 1980s by the third generation of catalysts. In the Ruhrchemie/Rhône-Poulenc (RCH/RP) process, water-soluble phosphine ligands enabled virtually loss-free recovery of the very expensive rhodium by phase separation of the aqueous catalyst solution from the organic product phase (DE-A-32 34 701, DE-A-32 35 030).

Water solubility of the catalyst is achieved by incorporation of one or a plurality of strongly polar group(s), such as —$SO_3H$, —COOH, —$NH_2$, or their salts, into the phosphine ligand. Development of the two-phase catalysis is therefore closely associated with the synthesis of such ligands.

Sulfonated phenylphosphines dissolve for instance in an aqueous medium at any pH value, while carboxylated phosphines only dissolve in acidic media. The hydrophilic character of triphenylphosphine (TPP) increases with an increasing number of sulfonic acid groups:

TPPMS<TPPDS<TPPTS=triphenylphosphinetrisulfonic acid (TPPMS=triphenylphosphinemonosulfonic acid, TPPDS=triphenylphosphinedisulfonic acid)

For industrial use, TPPTS is the ideal ligand for modifying the rhodium carbonyl species $HRh(CO)_4$. Without any elaborate synthesis, 3 of the 4 CO ligands can be replaced by the readily water-soluble, nontoxic TPPTS.

It is thus possible to provide tailored complex catalysts for a wide variety of applications.

The greatest advantage of water-soluble ligands is the ease with which the hydroformylation products can be separated from the catalyst. Homogeneous catalysts are usually separated from the product by thermal separation methods, such as distillation/rectification. This thermal stress can result in deactivation or even decomposition of the complex catalyst. In addition, loss-free recovery is not always possible. In the two-phase system of the RCH/RP process, the rhodium losses are in the ppb range.

In the reaction of synthesis gas with olefins, the hydroformylation can be accompanied by a series of secondary reactions, which influence conversion and selectivity. The hydrogenation of the olefinic double bond results in irreversible formation of saturated hydrocarbon and is likewise catalyzed by cobalt and rhodium. This parallel reaction reduces the aldehyde yield. With unmodified cobalt catalysts, hydrogenation is achieved to an extent of about 15%, based on the olefin quantity. When using modified rhodium catalysts, this reaction takes place to an extent of less than 5%. Follow-up reactions of the resultant aldehydes, e.g. condensation, trimerization, and aldol reaction, result in formation of heavy-end products having significantly higher boiling points than the desired products.

One of the main disadvantages of homogeneous catalysis can be avoided by two-phase catalysis. However, this reaction technique requires a minimum solubility of the olefins in water and is therefore restricted to short-chain olefins. Relatively long-chain olefins cannot be converted by this process. Such olefins are still hydroformylated homogeneously by a high-pressure process (Exxon process) over cobalt catalysts.

One possibility of reacting relatively long-chain olefins in a two-phase catalysis on rhodium complexes is the addition of phase-transfer catalysts or surfactants to the aqueous catalyst solution, thereby effecting micellar solubilization of the water-insoluble substrates. For this purpose, addition of cationic surfactants is reported to be preferable because cationic surfactant micelles not only solubilize the water-soluble olefin but also, as a result of their positive charge, bring about an accumulation of the negatively charged rhodium complex ions, thus increasing their concentration in the environment of the micelles (*Journal of Molecular Catalysis A: Chemical,* 101, 1995, p. 179–186).

Surfactant phosphanes combining the function of the surfactant for the micellar co-catalysis with that of the complexing ligand for the catalysis of the carbonylation reaction are also employed to that end (*Journal of Molecular Catalysis,* 66, 1991, p. 143–154).

Disclosed in U.S. Pat. No. 4,399,312 is a two-phase (aqueous phase/organic phase) hydroformylation reaction without formation of microemulsions. Reportedly, the addition of small amounts of amphiphilic reagents, such as ionic and nonionic surfactants with high HLB values, which are readily soluble in water, but sparingly soluble in oil, accelerates the materials transport without producing a microemulsion.

Nevertheless, the results when using phase-transfer catalysts or surfactants are not yet satisfactory in terms of reaction conditions and yields.

A new approach to a solution in the hydroformylation of long-chain olefins is the targeted reaction to form microemulsions.

Microemulsions are ternary mixtures of water, oil, and surfactant. The aqueous phase containing the catalyst is dispersed in the form of droplets in the oil phase, namely the olefin. At the phase boundary, catalyst, olefin, and dissolved synthesis gas meet and react to give the aldehyde.

EP-A-0 380 154 describes a hydroformylation process in which an olefin is reacted with hydrogen and carbon monoxide in the presence of a water-soluble hydroformylation catalyst in a microemulsion. The microemulsion comprises an oil phase made up of an olefin or an olefin and its hydroformylation products, an aqueous phase made up of the water-soluble complex catalyst, a surfactant, and a co-surfactant, with the oil phase forming the external phase of the microemulsion and the aqueous phase forming the internal phase. The co-surfactants which are most essential to form the microemulsion are preferably monohydric aliphatic alcohols having from 3 to 7 carbon atoms, in particular n-butanol or n-pentanol. Preferred surfactants are anionic ones, such as alkylbenzene-sulfonates or fatty alcohol sulfates.

A decided disadvantage of this process is the compelling addition of a co-surfactant the concentration of which must be checked because this concentration is responsible for formation of the desired microemulsion which should be stable up to conversion rates of 70%. Another problem is the fact that the co-surfactant partially accumulates in the product phase. Since it is preferable to use from 15 to 30% by weight of a co-surfactant in the hydroformylation reaction, this can lead to accumulation of considerable amounts of this agent in the product phase. This situation is undesirable because the short-chain alcohols which are preferably employed as a co-surfactant cause problems, e.g. regarding their odor, the undesirable secondary reactions (e.g. acetal formation with the aldehydes formed) which sometimes occur, and the adverse effect on the quality of the resultant long-chain hydroformylation products.

In view of the above description it is absolutely necessary to work up the product mixture further. Typical work-up procedures are, for example, removal of the undesirable co-surfactant, such as butanol, pentanol etc., from the product mixture by distillation and the acidic cleavage of the acetals formed from co-surfactant and aldehyde.

SUMMARY OF THE INVENTION

It is wherefore an object of the present invention to provide an improved process which does not have the aforementioned disadvantages.

It has now been surprisingly found that when using selected non-ionic surfactants, stable microemulsions can be obtained without employing any of the co-surfactants mentioned in EP 0 380 154.

According to the present invention, the problem is solved by a process for the catalytic hydroformylation of olefins by reaction of an olefin with hydrogen and carbon monoxide in a liquid, aqueous-organic medium in the presence of a water-soluble hydroformylation catalyst, characterized in that for a substantial period of the hydroformylation reaction, the aqueous-organic medium is present in the form of a microemulsion, which is made up of an oil phase containing the olefin or the olefin and its hydroformylation products, an aqueous phase containing the water-soluble catalyst complex, and a nonionic surfactant. Addition of a co-surfactant according to EP 0 390 154 is expressly omitted.

DESCRIPTION OF THE PREFERRED EMBODIMENTS

A clear advantage over the prior art process is the fact that the product phase in this case does not have to be worked up by distillation to remove the co-surfactant. Furthermore, checks of the co-surfactant concentration which is largely responsible for the formation of the microemulsion can be dispensed with.

As taught in EP 0 380 154, monohydroxy aliphatic alcohols having from 3 to 7 carbon atoms are used as co-surfactants.

According to another embodiment of this invention, the process for the catalytic hydroformylation of olefins in a liquid, aqueous-organic medium in the presence of a water-soluble hydroformylation catalyst is characterized in that for a substantial period of the hydroformylation reaction the aqueous-organic medium is present in the form of a microemulsion, which is made up of an oil phase containing the olefin or the olefin and its hydroformylation products, an aqueous phase containing the water-soluble catalyst complex, and one or a plurality of non-ionic surfactant(s), with at least one of these nonionic surfactants being an alkoxylated fatty alcohol. The nonionic surfactant is employed in quantities of from 5 to 30% by weight, based on the total formulation.

The alkoxylated fatty alcohol used according to the present invention has preferably 7 to 31 carbon atoms, more preferably 9 to 31, most preferably 9 to 18, referring to the fatty alcohol.

According to yet another embodiment, the alkoxylated fatty alcohols can have alkyl-terminal alkoxylate end groups and/or from 2 to 20 alkoxy units, preferably ethoxy units. It is preferable that narrow-distribution alkoxylated fatty alcohols be employed. Suitable products include for example Marlipal® $C_{13}$ products of CONDEA Chemie GmbH. Preferably, the nonionic surfactant consists of at least 50% by weight of an alkoxylated fatty alcohol as defined hereinabove.

In particular, the use of nonionic surfactants, which can be prepared in subsequent steps from the aldehyde formed in the hydroformylation reaction, is also advantageous. For example, the use of an $C_{13}$-ethoxylate is useful in the hydroformylation of tributene because the hydroformylation of tributene gives a $C_{13}$-aldehyde which is converted by hydrogenation and ethoxylation into an $C_{13}$-ethoxylate. This surfactant has the advantage that part thereof can remain as an impurity in the hydroformylation product. There is no impairment of quality of the resultant product if a certain amount of the nonionic surfactant is still present in the product mixture of the hydroformylation reaction.

Furthermore, it has surprisingly been found that it is not imperative to carry out the reaction in a single-phase microemulsion but that the hydroformylation can also be performed in a two-phase system consisting of a microemulsion, which is in contact with an olefin phase serving as a reservoir, with the yields and selectivities remaining unchanged. It appears that the only prerequisite for a satisfactory reaction rate is a sufficient olefin concentration at the internal phase boundary of the microemulsion. This specific variant of the reaction procedure offers further advantages. Said system allows to separate the phases and recycle the catalyst without changing the temperature. Moreover, this two-phase area including microemulsion and olefin phase exists for a prolonged period of the hydroformylation reaction.

In a preferred embodiment, the products prepared by the process of the invention are subjected to ultrafiltration to separate small amounts of rhodium or rhodium complexes, thereby further reducing the loss of noble metal.

Suitable olefins include linear or branched olefins having from 2 to 30 carbon atoms, particularly from 6 to 30, most particularly from 8 to 12. The olefinic double bond can be a terminal one (α-olefins) or an internal one.

The catalysts employed in the process as claimed herein are preferably rhodium compounds containing water-soluble, complexed phosphines, i.e. salts wherein the anion is a phosphine containing at least one sulfonated or carboxylated group. Particularly preferable as complex ligands are phosphines containing aromatic radicals, in particular sulfonated triarylphosphines. In general, it is possible to use not only rhodium compounds but also any other metal compound selected from among hydroformylation-active transition metal compounds, such as cobalt, ruthenium, osmium, iridium, palladium, and platinum.

The hydroformylation catalysts are prepared by combining the transition metals or their compounds (e.g. complexes) with ths water-soluble phosphine ligands in an aqueous medium. The water-soluble phosphine ligands should be used in excess, i.e. in a significantly larger quantity than the stoichiometric moiety. In principle, the catalyst can also be added in a preformed condition to the reaction system.

The nonionic surfactant used in the hydroformylation is preferably selected from the group consisting of alkoxylated fatty alcohols, particularly ethoxylated ones, alkoxylated alkylphenols, fatty acids or fatty acid esters, fats, oils, and waxes.

The hydroformylation reaction can be carried out continuously or discontinuously. Desirably, the process of the invention is conducted at reaction temperatures in the range from 40 to 150° C. and reaction pressures in the range from 2 to 150 bar.

The reaction is preferably carried out at temperatures of from 50° C. to 100° C. and pressures of from 20 to 60 bar. The molar feedstock ratio (hydrogen:carbon monoxide) can be varied within wide limits. In general, a synthesis gas is employed, wherein the carbon monoxide:hydrogen volume ratio is from 1:1 to 1:1.5.

EXAMPLE 1

2.3 grams of an aqueous solution containing 44 grams/liter of tris-(3-sulfophenyl)-phosphine trisodium salt (Sigma-Aldrich) and 5 grams/liter of di-$\mu$-chloro-bis-[(cycloocta-1c,5c-diene)-rhodium (I)] were added at room temperature to 22.7 grams of n-dodecene-1 (Sigma-Aldrich). In addition, 3.8 grams of Marlipal® $C_{13}$/70 ($C_{13}$-oxoalcohol polyethyleneglycolether (7 EO), CONDEA Chemie GmbH) were added to this two-phase system. Formation of the microemulsion was confirmed by examining the phase behavior in a constant-temperature bath. The resultant microemulsion had the following composition (as percentages by mass):

| | |
|---|---|
| n-dodecene-1 | 79% |
| Marlipal ® $C_{13}$/70 | 13% |
| Aqueous catalyst solution | 8% |

The microemulsion was transferred to a 100-ml lab-scale autoclave and heated to 75° C. The pressure of the synthesis gas (hydrogen:carbon monoxide ratio: 1:1) was increased to 30 bar. Under these conditions, the reaction mixture was stirred for 10 hours. The autoclave then was cooled and depressurized, and the reaction mixture was discharged. The mixture separated into two phases: an upper oil-rich phase containing n-tridecanal, iso-2-methyldodecanal, and unreacted n-dodecene-1; and a lower aqueous phase containing the catalyst and the major portion of the surfactant. GC analysis indicated an olefin conversion of 61% and a conversion into aldehyde (both n- and iso-aldehyde) of 61%. Hence, the selectivity to aldehyde was 98.3%. The ratio of n-aldehyde to iso-aldehyde was 2.74.

EXAMPLE 2

The same procedure was adopted as in Example 1, except that the pressure of the synthesis gas was adjusted to 50 bar.

After a reaction time of 10 hours, the olefin conversion was 77.6%, while the conversion into aldehyde was 74.7%. Hence, the selectivity to aldehyde was 96.2%. The ratio of n-aldehyde to iso-aldehyde was 1.73.

EXAMPLE 3

The rhodium salt employed for preparing the catalyst was $Rh(CO)_2(acac)$. The reaction was carried out as described in Example 1, except that the pressure of the synthesis gas was adjusted to 100 bar. After a reaction time of 10 hours, the olefin conversion was 90.5%, while the conversion into aldehyde was 90.3%. Hence, the selectivity to aldehyde was 99.8%. The ratio of n-aldehyde to iso-aldehyde was 2.3.

EXAMPLE 4

Tributene (technical-grade isomers mixture) was converted as described in Example 1, except that the pressure of the synthesis gas was adjusted to 80 bar. After a reaction time of 10 hours, GC analysis indicated an olefin conversion of 69.6%. Since the isomers quantity was high, the selectivity could not be determined.

What is claimed is:

1. A process for the catalytic hydroformylation of olefins in a reaction mixture comprising a liquid, aqueous-organic medium in the presence of a water-soluble hydroformylation catalyst, characterized in that for a substantial period of the hydroformylation reaction, the aqueous-organic medium is present in the form of a microemulsion, which is made up of an oil phase containing the olefin or the olefin and its hydroformylation products, and an aqueous phase containing the water-soluble complex catalyst, and at least one nonionic surfactant, wherein at least one of the nonionic surfactants is an alkoxylated fatty alcohol and the nonionic surfactant is employed in quantities of from 5 to 30% by weight, based on the total reaction mixture and wherein addition of a monohydroxy aliphatic alcohol having from 3 to 7 carbon atoms as a co-surfactant is omitted.

2. The process according to claim 1, characterized in that the alkoxylated fatty alcohol has from 7 to 31 carbon atoms, referring to the fatty alcohol.

3. A process according to any one of claims 1, or 2, characterized in that for a substantial period of the hydroformylation reaction, the aqueous-organic reaction medium is present as a two-phase mixture comprising a microemulsion in equilibrium with an olefin-rich phase.

4. A process according to any one of claims 1, or 2, characterized in that hydroformylation catalyst is separated by ultrafiltration.

5. A process according to any one of claims 1, or 2, characterized in that the oil phase contains a linear or branched olefin selected from the group consisting of alpha-olefins having from 6 to 30 carbon atoms, internal olefins having from 6 to 30 carbon atoms, and mixtures thereof.

6. A process according to any one of claims 1, or 2, characterized in that the aqueous phase contains a dissolved, water-soluble complex catalyst, which is made up of a water-soluble phosphine and a metal, a water-soluble compound, or a water-soluble complex of a hydroformylation-active metal.

7. A process according to claim 6, characterized in that the water-soluble phosphine is a sulfonated phosphine.

8. A process according to any one of claims 1, or 2, characterized in that the hydroformylation-active metal in the complex catalyst is selected from the group consisting of cobalt, ruthenium, rhodium, palladium, osmium, iridium, platinum, and mixtures thereof.

9. A process according to any one of claims 1, or 2, characterized in that the nonionic surfactant is selected from the group consisting of alkoxylates of fatty alcohols, alkylphenols, fatty acids or fatty acid esters, fats, oils, waxes, and mixtures thereof.

10. A process according to claim 9, characterized in that the alkoxylates are ethoxylates.

11. A process according to any one of claims 1, or 2, characterized in that the nonionic surfactant is at least one alkyl-terminal alkoxylate of a fatty alcohol.

12. A process according to any one of claims 1, or 2, characterized in that the nonionic surfactant is at least one narrow-distribution ethoxylate of a fatty alcohol.

13. A process according to any one of claims 1, or 2, characterized in that at least one of the nonionic surfactants can be prepared from the aldehyde formed in the hydroformylation reaction.

14. A process according to any one of claims 1, or 2, characterized in that the reaction temperature is in the range of from 40 to 150° C. and the reaction pressure is in the range of from 2 to 150 bar.

15. A process of claim 1, characterized in that the alkoxylated fatty alcohol has from 9 to 31 carbon atoms, referring to the fatty alcohol.

* * * * *